United States Patent
Horowitz et al.

(10) Patent No.: US 10,360,810 B1
(45) Date of Patent: *Jul. 23, 2019

(54) EDUCATIONAL DOLL FOR CHILDREN WITH CHRONIC ILLNESS

(71) Applicant: SPROUTEL INC., Providence, RI (US)

(72) Inventors: Aaron Jay Horowitz, Providence, RI (US); Hannah Chung, Providence, RI (US); Mert Hilmi Iseri, Evanston, IL (US); Yuri Frank Maxwell Malina, Evanston, IL (US)

(73) Assignee: SPROUTEL INC., Providence, RI (US)

( * ) Notice: Subject to any disclaimer, the term of this patent is extended or adjusted under 35 U.S.C. 154(b) by 445 days.

This patent is subject to a terminal disclaimer.

(21) Appl. No.: 15/202,057

(22) Filed: Jul. 5, 2016

Related U.S. Application Data

(63) Continuation of application No. 13/630,524, filed on Sep. 28, 2012, now Pat. No. 9,390,626.

(Continued)

(51) Int. Cl.
| | |
|---|---|
| *G09B 19/00* | (2006.01) |
| *G09B 5/00* | (2006.01) |
| *G09B 5/02* | (2006.01) |
| *G09B 5/04* | (2006.01) |
| *G16H 50/50* | (2018.01) |
| *G09B 23/28* | (2006.01) |
| *G09B 23/30* | (2006.01) |
| *A63H 33/30* | (2006.01) |
| *A63H 3/00* | (2006.01) |
| *A61B 5/0215* | (2006.01) |

(52) U.S. Cl.
CPC ............... *G09B 19/00* (2013.01); *G09B 5/00* (2013.01); *G09B 5/02* (2013.01); *G09B 5/04* (2013.01); *A61B 5/0215* (2013.01); *A63H 3/001* (2013.01); *A63H 33/3094* (2013.01); *G09B 23/28* (2013.01); *G09B 23/285* (2013.01); *G09B 23/30* (2013.01); *G16H 50/50* (2018.01)

(58) Field of Classification Search
CPC ...... G09B 23/28; G09B 23/285; G09B 23/30; G09B 19/00; G09B 5/00; G09B 5/02; G09B 5/04; G16H 50/50; A61B 5/0215; A63H 33/3094; A63H 3/001
USPC .......................................................... 434/262
See application file for complete search history.

(56) References Cited

U.S. PATENT DOCUMENTS

| | | |
|---|---|---|
| 2,774,184 A | 12/1956 | Hefferan et al. |
| 4,075,782 A | 2/1978 | Neuschatz |

(Continued)

*Primary Examiner* — Jack Yip
(74) *Attorney, Agent, or Firm* — Drinker Biddle & Reath LLP

(57) ABSTRACT

An interactive toy serving as a surrogate by emulating chronic condition characteristics of a child and providing responses and output to educate user about the chronic condition. The toy may include a microprocessor and memory, and a plurality of sensors that receive information representative of a treatment for the chronic condition and output systems that simulate reaction to the treatment of the chronic condition. The toy may include a plurality of replica food articles that interact with the sensors and the output systems. The toy may further include a plurality of replica or real medical devices that interact with the sensors to simulate reaction to treatment via the output systems.

21 Claims, 5 Drawing Sheets

Related U.S. Application Data

(60) Provisional application No. 61/539,978, filed on Sep. 28, 2011.

(56) References Cited

U.S. PATENT DOCUMENTS

| | | | |
|---|---|---|---|
| 4,601,668 A | 7/1986 | Sirota | |
| 4,737,131 A | 4/1988 | Sirota | |
| 4,740,186 A | 4/1988 | Sirota | |
| 4,917,607 A | 4/1990 | Van Hoose | |
| 5,004,136 A | 4/1991 | Leath | |
| 5,037,302 A | 8/1991 | Sirota | |
| 5,094,621 A | 3/1992 | Friedel | |
| 5,312,887 A | 5/1994 | Papathomas | |
| 5,514,117 A | 5/1996 | Lynn | |
| 5,842,870 A | 12/1998 | Cramer | |
| 6,544,041 B1* | 4/2003 | Damadian | G09B 23/285 434/262 |
| 7,547,278 B2 | 6/2009 | Miyazaki et al. | |
| 8,313,330 B2 | 11/2012 | Maspoli et al. | |
| 2002/0168618 A1* | 11/2002 | Anderson | A61F 2/07 434/262 |
| 2004/0161732 A1 | 8/2004 | Stump et al. | |
| 2004/0197764 A1 | 10/2004 | Stump et al. | |
| 2005/0277096 A1* | 12/2005 | Hendrickson | G09B 23/285 434/262 |
| 2007/0117075 A1* | 5/2007 | Gordon | G09B 23/28 434/262 |
| 2011/0306025 A1* | 12/2011 | Sheehan | A61B 8/523 434/267 |
| 2012/0288837 A1* | 11/2012 | Eikefjord | G09B 23/28 434/262 |
| 2014/0058709 A1* | 2/2014 | MacHado Viana | G01M 5/0033 703/2 |

\* cited by examiner

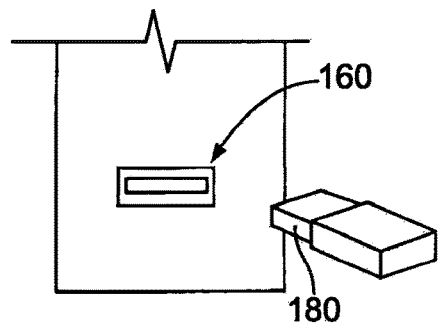 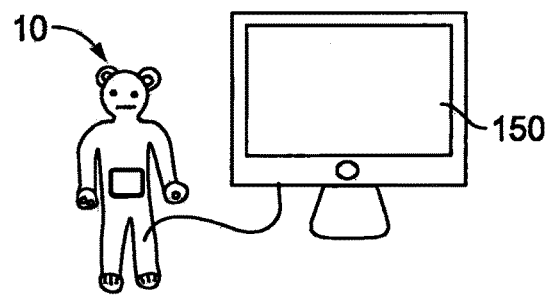
FIG. 9A          FIG. 9B
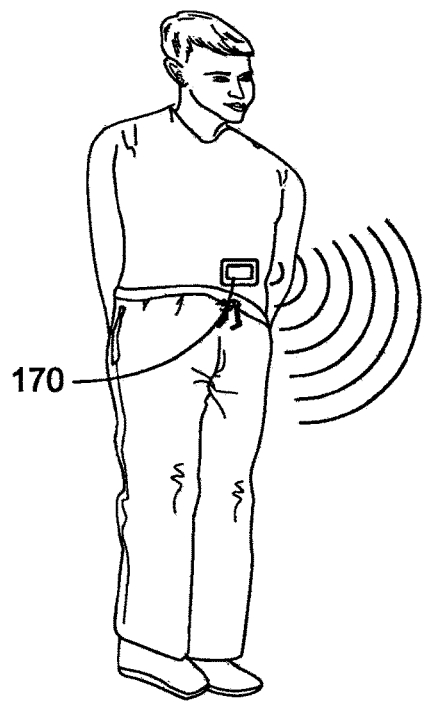 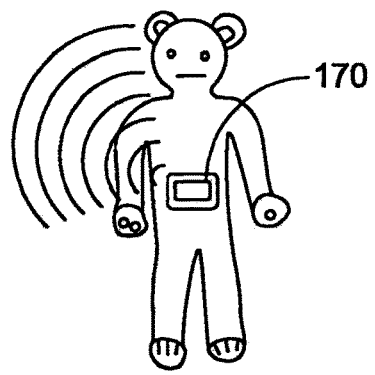
FIG. 10

EDUCATIONAL DOLL FOR CHILDREN WITH CHRONIC ILLNESS

CROSS-REFERENCE TO RELATED PATENT APPLICATIONS

The present application is a continuation of U.S. patent application Ser. No. 13/630,524 filed Sep. 28, 2012, to issue as U.S. Pat. No. 9,390,626 on Jul. 12, 2016, which claims the benefit of U.S. Provisional Patent Application No. 61/539,978 filed Sep. 28, 2011. Both of the above-referenced applications are herein incorporated by reference in their entirety.

TECHNICAL FIELD

Disclosed herein are educational interactive feedback systems and devices, particularly those for educating children with a chronic illness and their parents on behavioral compliance.

BACKGROUND

For young children, living with a chronic illness can be very difficult. In addition to dealing with the mental stresses of serious medical treatment and loneliness, these children must also face, on a daily or hourly basis, a variety of medical procedures. Both children and their parents must regularly practice and perform these procedures to maintain the well-being of the child. Children suffering from chronic illnesses must learn to live with many devices that monitor their health and manage their symptoms. Although these conventional devices are critical to maintaining the child's health, children often view them as invasions of personal space and frequently see the devices as unwanted foreign objects.

Children with chronic illnesses are unprepared to manage their illnesses on a daily basis and are therefore likely to suffer medical crises. These crises can be avoided by gaining a fuller understanding of the chronic illness. Education for the child-patient and the parents is critical to proper management of the child's disease. Parents, and especially their children, must become active participants in the treatment of their disease.

These children are often not allowed to practice their own medical procedures, which can be critical to their lives. Until now, they lack a method to gain hands on experience in mastering their disease and, as a result, they must take a passive role in their own care, deferring to parents, teachers, and other care takers to practice the medical procedures that are so critical to their well being.

For a child with a chronic illness, behavior modifications early in life can lead to immense health savings later on. It is currently difficult to make children aware of the ramifications of their unhealthy behaviors and as a result typical methods revert to scare tactics and statistics aimed at parents.

Most parents and children lack health education and medical training, and outpatient care is conventionally limited to brief interactions with physicians and assistants at treatment centers. For parents, learning that they will have a huge amount of medical responsibility due to their child's illness can be unnerving. Further, both the child and the parents must learn a huge amount of information that is critical to the child's well-being, and trying to absorb this array of information can be overwhelming. Children and parents must enforce dietary restrictions, closely follow medication schedules, attend frequent physician visits, and administer routines of injections. Children and parents must also keep up-to-date on any changes in these regimens and incorporate them immediately into their routines.

Providing medical education via a hands-on method increases the chances for correct care in the same scenario in real life. This enables those children who cannot yet practice procedures on themselves to learn proper care practices in a safe environment that prepares them for realistic potential scenarios.

Providing medical education in a relaxed atmosphere for parents increases the likelihood of information retention. Further, interacting with the child through playtime exercises, for example with a doll, can spur information retention by creating a fun and nurturing atmosphere. Thus, there is a need for medical education for both children and parents that is provided in a relaxed atmosphere where the child can play with an inanimate object. This education may teach children and parents how to perform the actions necessary to maintain the health of the child. Providing the education in this manner may also help the child mentally cope with the stresses of having a chronic illness, including helping the child overcome feelings of loneliness and isolation created by the chronic illness. If the child learns that the doll suffers from the same affliction as the child, the child may feel compassion and share a bond with the doll. Features increasing the humanism of the doll such as a glowing or pulsating heart and a heat generating unit may increase the child's connection to the doll and encourage the child to medically treat the doll and learn about its illness.

SUMMARY

Embodiments of the invention provide an interactive toy that a child afflicted with a chronic illness may use to learn about and help manage that illness. The toy may take the shape of a doll or animal and may be plush or hard. The toy may have a plurality of sensors connected via wires to an internal microprocessor or via wires or wirelessly to an external processor. The toy may also include a detachable core unit containing a microcontroller, a plurality of batteries, and a plurality of sensors. The detachable core may include a pedometer that the child may use to monitor exercise. The toy may further encourage exercise and healthy habits specific to a child's chronic illness through a variety of visual and auditory stimuli. Further included in the toy may be a feedback system such as a screen or visual display connected to the microprocessor that may display information regarding treatment conditions and the state of the toy, among other things. Further included in the toy may be a feedback system consisting of an audio speaker connected to the microprocessor that may provide audio feedback to the child or other users. A feedback system comprising a motor generating vibrational or translational movement of the toy may also be included.

The toy may work with both real and replica medical equipment. For example, the child patient may be able to check the toy's health state with a real blood glucose meter, or the child patient may be able to administer a dosage of medication to the toy with an actual metered dose inhaler. Likewise, the toy may recognize via proximity, touch, or other detection methods that the replica medical equipment is performing a medical treatment on the toy. These detection methods non-exclusively include RF, magneto-inductive, or optical methods known in the art. Medical equipment may also include metered-dose inhalers, dry powder inhalers, nebulizers, analgesic inhalers, syringes, stethoscopes, gastric feeding tubes, insulin pumps, glucose monitoring systems, and the like. Further still, the toy may detect treatment by detecting the color or other attributes, such as weight, size, shape, or composition of replica food or pills administered through the toy's mouth opening. The toy may respond to these actions and provide visual, auditory, or motive feedback generated and controlled by the microprocessor within the toy. The toy's responses to stimuli may evolve over time. Among other things, the toy's responses may become more demanding or rigid as the user adapts to and learns about the illness.

Included with the toy may be embodiments of the invention comprising a practice medical kit including the real or replica medical equipment, and also including a book describing aspects of the required medical treatment. This book may be an interactive electronic book and it may be a conventional book serving as a reference. The book may also be linked wirelessly or via wires to the toy such that the toy may broadcast aloud portions of the book's contents. The contents of the book may also be loaded into the toy for native playback.

The toy is educational and can also serve to garner a child's affection. For example, in an embodiment of the system, a child may care for the toy like a mother and develop a nurturing relationship.

The toy may also provide education on maintaining a healthy diet in accordance with medically standard treatment for a plurality of chronic illnesses. For example, educating children and parents about type 1 diabetes includes educational information on counting carbohydrates.

The toy may also educate children about proper usage of applicable medical devices including teaching diabetic children how to use insulin pumps, injection pens, and continuous glucose monitors. Embodiments of the invention can teach asthmatic children to properly use their inhalers.

The toy may also socially connect children who have a chronic illness. Children diagnosed with a chronic illness often become lonely. Embodiments of the invention seek to connect these children with others suffering from the same illness.

The toy may also track compliance of medical procedures for later analysis and/or transmission to a doctor or caretaker. Embodiments the invention may also act as a gateway, transmitting data from actual medical devices, such as blood glucose meters and insulin pumps, to the web to be viewed by parents and medical professionals.

The toy may also record data from a child's external medical device to track compliance with medical procedures. Embodiments of the invention can connect (by wired or wireless means) to an external computer to sync data recorded from the child's toy.

The toy may also educate the child about injection rotation to avoid negative side effects including scar tissue and reduced medication uptake.

The toy may also exhibit symptoms of the chronic illness both visually, audibly, and through touch sensory (haptics, vibrating motor, etc.) to educate children about potential consequences of the disease and its treatment or lack thereof.

An embodiment of the system can include a toy having a head, torso, arms, and legs. A screen, internally illuminated extremities, buttons, and a plurality of injection sites may be disposed at various locations of the body. The injection sites may be coded with symbols to differentiate between injection sites and facilitate education regarding injection site rotation. A food differentiation system may be located in the head. In this embodiment, the hands of the toys have sensors that detect proximity and replicate a medical test when triggered.

Embodiments of the invention provide a toy, real or replica medical equipment, and a manual. The toy may take the form of a stuffed animal or other figure. Embodiments may be directed to children with chronic illnesses and their parents. These users may learn health management techniques through interaction with the toy. The child or parent may practice performing the child's medical treatment on the toy using the real or replica medical equipment. Those users may then receive feedback from the toy, enhancing the learning process.

The toy included in embodiments of the invention may use a microprocessor and software that can execute commands to provide feedback to the users. For example, the microprocessor may control an audio output device consisting of a speaker system or a device with similar functionality known in the art. As a further example, the microprocessor may command a display screen that may, for example, instruct the user on the proper administration of treatment.

The microprocessor used with the toy may be a general purpose processor, an application specific processor, a FPGA, or a similar device known in the art. The microprocessor may be reprogrammable or the software running on the processor may be reprogrammable. By reprogramming the device, it may be updated, customized, and re-used. The toy may also contain a memory interacting with the processor conforming to the standards of RAM, RDRAM, SDRAM, DRAM, VRAM, or other types of volatile or non-volatile memory known in the art.

The toy included in embodiments of the invention may use sensors and input devices that may help the user interact with the toy. The sensors may be activated in response to sounds, touch, and the presence or absence of replica or real medical equipment.

The replica or real medical equipment that may be used with the invention may include metered-dose inhalers, dry powder inhalers, nebulizers, analgesic inhalers, syringes, stethoscopes, gastric feeding tubes, insulin pumps, and glucose monitoring systems, among other things. The medical equipment listed is not exhaustive. Different medical equipment known in the art may be required to educate the child and parents on varying diseases.

Embodiments of the invention may be compatible and adaptable to many different illnesses afflicting children. For example, the number, location, and type of sensors may be modifiable to support multiple illness treatments. Likewise, the processor and software may be adaptable to multiple different illnesses and may provide appropriate feedback given the illness selected.

For individuals who receive injections daily, rotation of injection sites is critical so that scar tissue does not build up and prevent absorption of injections. Embodiments of the invention may have a plurality of injection sites that may be used to practice rotating injection sites. The injection sites may be labeled with symbols to assist the child in differentiating between injection sites and aid injection rotation of those sites.

Embodiments of the invention may also educate users on diet management techniques. Users may present the toy with various replica food articles, and the toy may detect the type of food and the nutritional and dietetic impact for a disease.

Embodiments of the invention may perform a staged process of educational content delivery, delivering more information to the child and parents after mastery of previously delivered information is exhibited. Staged content delivery may also enhance the interactive nature of the device.

Embodiments of the invention may also interface with a personal computer or mobile device through a wired or wireless connection. Information about health care compliance may be recorded and feedback regarding compliance may be provided through these or other mechanisms. By interfacing with a PC or mobile device, play can also be continued from the real world to the virtual world.

Embodiments of the invention may emit multi-colored light from one or more extremities of the system. This light may provide feedback to users regarding treatment conditions. The toy may also provide a glowing, pulsating, or audibly beating heart.

In order to educate users on diet management, embodiments of the invention may use a novel color sensing system.

Embodiments of the invention may help a child cope with a variety of chronic illnesses including asthma, allergies, cystic fibrosis, diabetes, cancer, cerebral palsy, sickle cell anemia, AIDS, epilepsy, spina bifida, pulmonary hypertension, sleep apnea, liver cirrhosis, hyperthyroidism, chronic obstructive pulmonary disease, and congenital heart problems.

BRIEF DESCRIPTION OF DRAWINGS

The following drawings illustrate an embodiment of the invention that is described in more detail below.

FIG. 9A is a perspective view of removable storage media interfacing with a computer;

FIG. 9B is a perspective view of the toy directly interfacing with a computer system; and FIG. 10 is a perspective view of the toy wirelessly communicating with an individual wearing a remote communication module.

DETAILED DESCRIPTION OF THE EMBODIMENTS

Figure 1:
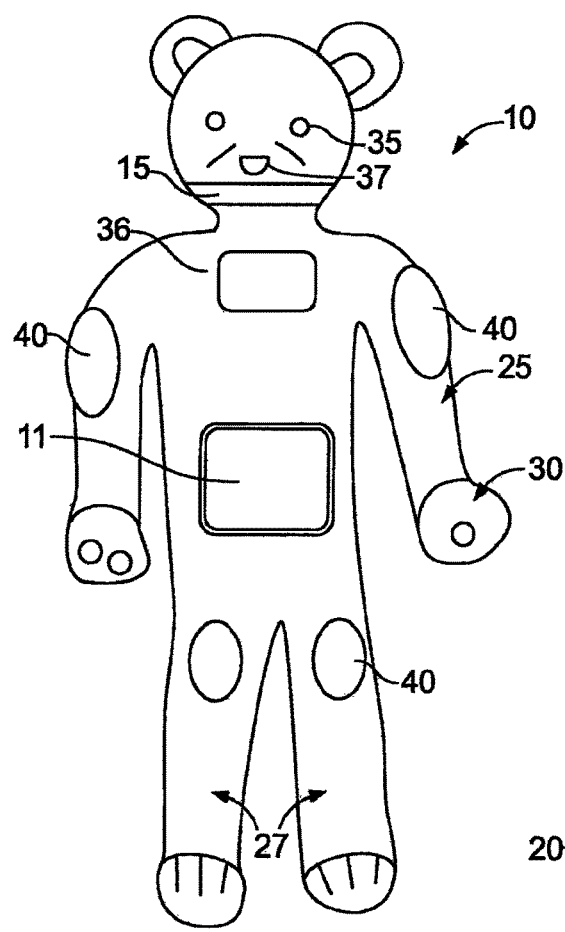
FIG. 1 is a front view of the toy corresponding to one embodiment of the invention.
Figure 2:
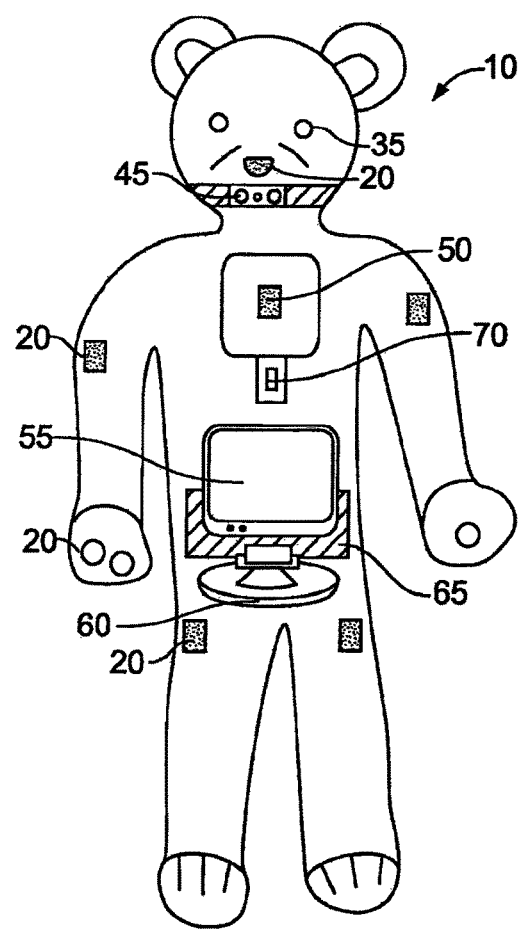
FIG. 2 is a front partial cut-away view of the toy corresponding to one embodiment of the invention.

An embodiment of the invention will now be described with reference to the accompanying drawings. Referring to FIGS. 1 and 2, the toy 10 may have a slotted mouth opening 15, and proximity sensors 20 or switches 22 located on the arms 25, hands 30, legs 27 and eyes 35. The proximity sensors 20 in the arms 25 may be injection sites, and they are activated by a replica injection pen 110. The proximity sensors 20 in the hands 30 may represent sites that are triggered when touched, or activated with a replica lancet, to "read" the blood glucose level or internal state of the toy 10. Similarly, proximity sensors 20 may be located on the legs 27 of the toy 10. Embodiments of the toy 10 may be plush or hard bodied. Embodiments of the toy 10 may resemble a person or animal having a head, torso, arms, and legs, but may also embody other objects as well.

Embodiments of the toy 10 may include a proximity activated color sensor 45 located within a slotted mouth opening 15, as well as a motion sensor 70 attached to the internal surface of the toy. Such a proximity activated color sensor 45 can be used to sense and distinguish different types of replica or real food objects. For example, sensing a yellow color can determine the presence of a banana. Other replica food items may have a specific color that is sensed by the color sensor 45. Other types of sensors or imaging devices may be used as well. These sensors may be connected via internal wires or wirelessly to a microprocessor 50, an audio speaker 60, actuators and screen 55 connected to the internal microprocessor 50, whereupon activation of the microprocessor 50, the toy 10 produces a programmed response. For example, one actuator may be an LED that produces a glowing nose of the toy, which may glow in different color to indicate various internal states of the toy.

Figure 3:
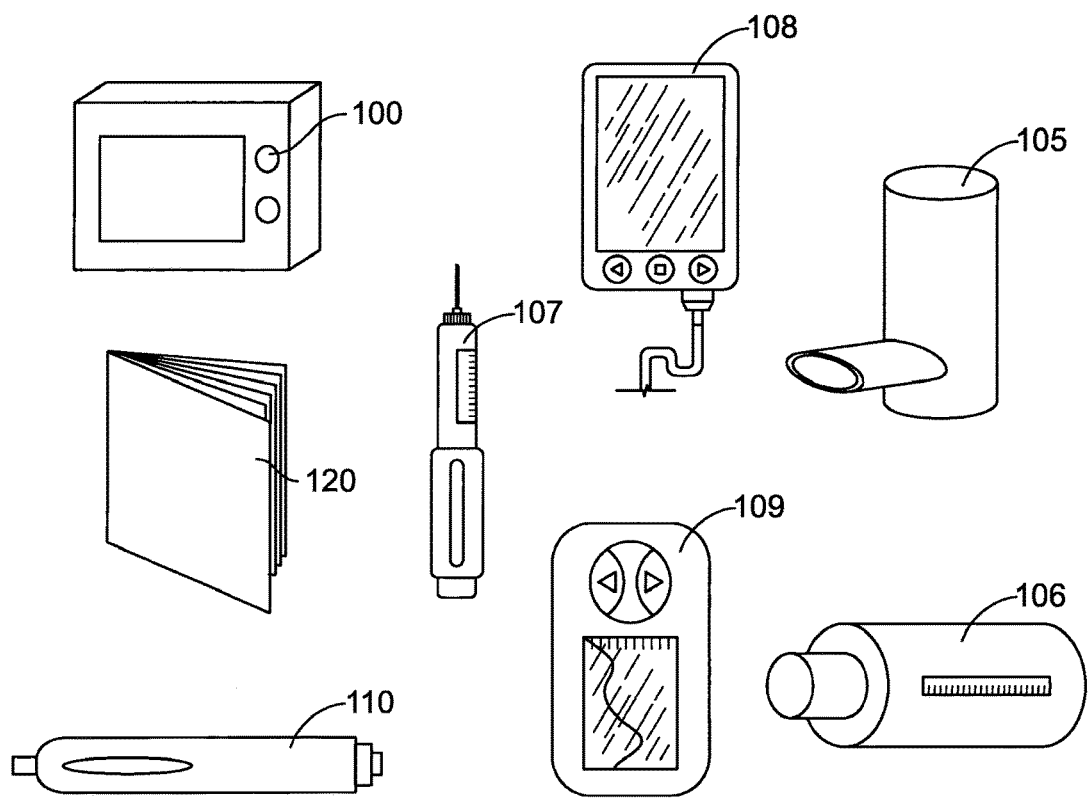
FIG. 3 is a perspective view of accessories that may be used with embodiments of the invention.
Figure 4:
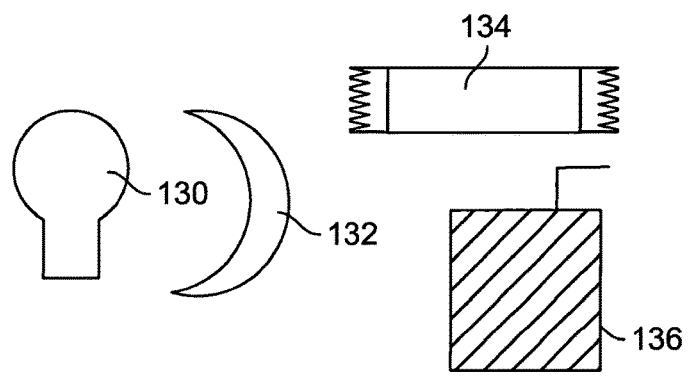
FIG. 4 is a perspective view of replica food articles used with embodiments of the invention.
Figure 5:
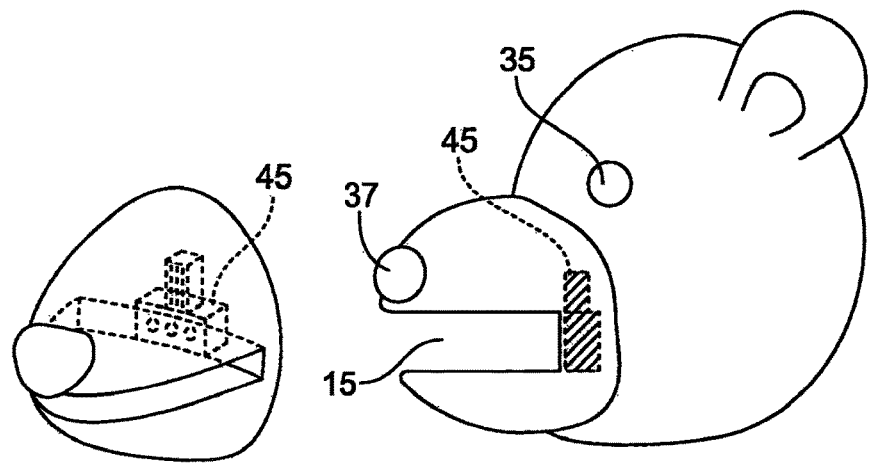
FIG. 5 is a side view of a replica food article being inserted into the mouth of the toy.
Figure 6A:
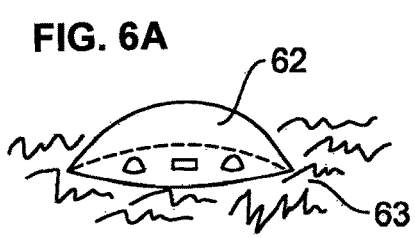
FIG. 6A is a side view of an injection site on the toy.
Figure 6B:
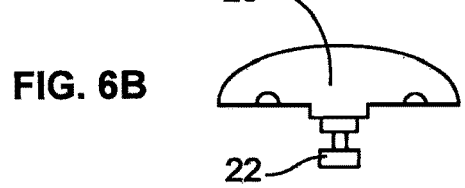
FIG. 6B is a side view of an injection site not connected to the toy.
Figure 6C:
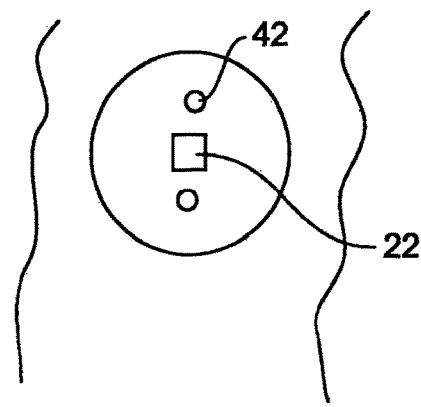
FIG. 6C is a top view of an injection site connected to the toy.

Referring to FIG. 3, the toy may include and interact with one or more replicas of medical devices including a glucometer 100, an injection pen 110, a flow control meter 106, an insulin pen 107, and insulin pump 108, a CGM meter 109, or an inhalor 105. Referring to FIG. 3, the toy may further include and interact with an instruction manual or story book 120, and FIG. 4 shows objects representing replica food items including bread 130, bananas 132, candy bars 134, and juiceboxes 136.

An embodiment may include one or more medical devices or replicas thereof with exemplary devices shown in FIG. 3. Instruction on use of these medical devices may be represented on a screen 55 (FIG. 1) located on the torso of the toy 10 and connected to the internal microprocessor 50. Buttons or proximity switches 22 may be disposed on or within the body of the toy 10 in a plurality of locations to provide user interaction with the toy 10. A method performed by the toy can provide through the form of text displayed on the screen 55, audio commands played through the audio speaker 60, and in an accompanying instruction manual or story book 120 on how to effectively and properly interact with the toy 10.

Patches 40 (FIG. 1) may be disposed at a plurality of locations along the external surface of the toy 10, with proximity sensors 20 located beneath the patches 40. Additionally, a replica of an injection pen 110 may be used which activates the proximity sensors 20, sending a signal to the microprocessor 50 which in response produces a pre-programmed response. Text on the screen 55, audio commands, as well as digital media tools may help educate users about proper injection site rotation.

Additionally, patches may feature a lighting element 42 and a switch 22 enabling them to display as different colors and function as buttons. This can be used as a method for education, and also as a game that children can play. The system may display a pattern of colors using the patches, and the child will then be asked to repeat the pattern by either touching the patches or using the included injection pen. The patches may also be marked with symbols aiding the differentiation between the patches and therefore aid injection site rotation.

The toy 10 may be programmed to perform a method for educating about diet management, comprising either an included book, an interactive e-book, a computer application, or a mobile application. The instructions may be displayed on the screen 55, and associated audible commands are emitted from the system. Through this method, information can be provided, for example, about how certain foods can contribute to well-being and how certain foods can induce symptomatic responses due to a chronic illness.

Figure 7A:
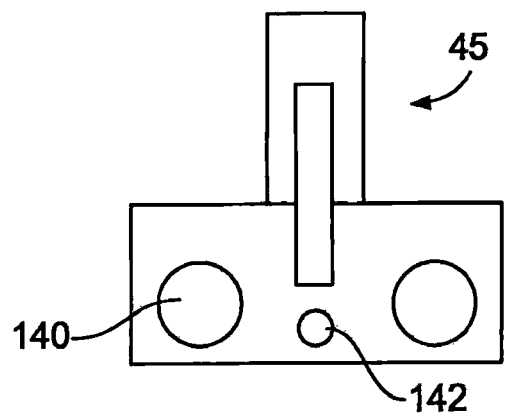
FIG. 7A is a front view of the food identification sensor.
Figure 7B:
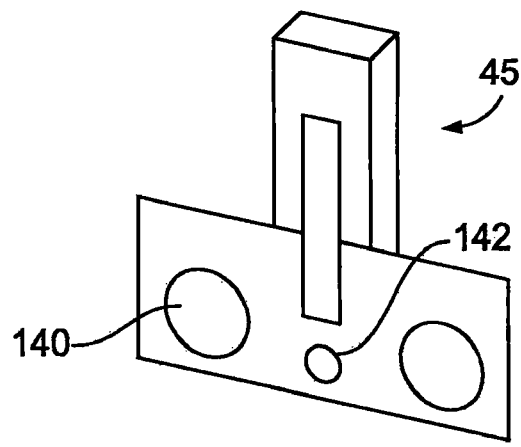
FIG. 7B is a perspective view of the food identification sensor.
Figure 8:
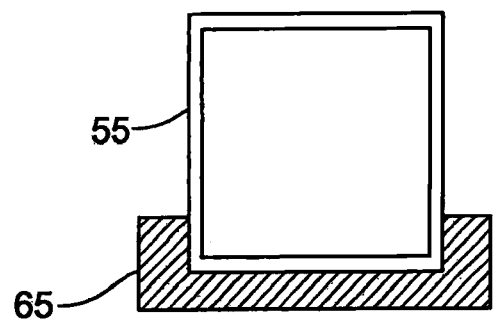
FIG. 8 is a front view of the screen detached from the toy.

In one embodiment the toy may include a slot 15 located on the external surface which represents a mouth. A plurality of replica food articles (FIG. 4), each of a different color, may be inserted into the slot 15, a proximity switch 20 (FIG. 1) will be activated sending a signal to the microprocessor 50 to initiate the color sensing routine. Using red, green and blue illumination 140 (FIG. 7) and a light sensor 142, the replica food article color is then detected and a pre-programmed response is initiated by the microprocessor, which may yield an audio response as well as a visual response utilizing the screen and colored light. Other means of food identification and differentiation are possible within the system including, olfactory, visual, audio, tactile, radio frequency (Bluetooth, NFC, RFID), haptic, or any other methods apparent to one skilled in the art.

This same mechanism of identification could also be used to educate children about oral medications such as the correct dosage of an inhaler or pill by having inhalers of different colors representing different doses, and different color pills representing different medications.

The system will produce a programmed response corresponding to symptoms of the chronic illness, as well as exhibit behavior indicative of the response using one or more actuators 22, light, and/or a vibrational motor 62 located within the toy.

The system will produce written text, programmed responses, audio feedback, touch (vibration motor, haptic feedback, etc. . . . ) and color recognition as tools for teaching children about chronic illnesses. The combination systematically creates a positive feedback mechanism that relays the critical points of the illness to the child.

Disposed within the internal surface of the toy 10 may be one or more motion sensors 70 to measure movement, position or motion. The motion sensor 70 is used to trigger audio/visual responses when the toy is being used. The motion sensor 70 is also used to track exercise and its effect on the system's chronic illness. Such motion sensors can be any of a variety of available sensors, using piezo-electric or other sensing approaches.

The toy can connect with existing medical equipment to add functionality as illustrated by way of example in FIGS. 9 and 10, which may include data collecting, compliance tracking and/or providing information to medical professionals about the child with a chronic illness. For example, a child with diabetes may be able to sync his or her Continuous Glucose Monitoring (CGM) device with the toy to update the glucose level information in the system. Using accompanying software, the child will be able to digitally log his or her own compliance for future records and usage.

A suite of software 40 (FIG. 9) may be provided to interface with the toy to transfer responses and stored information to a computer via a port 37, or potentially wireless means, located in the toy. The software is interactive and the toy's responses can be monitored and medical professionals and family members can track the toy's and child's health status. The toy may include software programmed to perform a game where children can learn more about chronic illnesses and their treatments. The software may further include links to websites where children may have easy access to health information, and facilitate real time online discussions with a medical professional so that children may ask questions. This functionality may also allow children to interact with other children with chronic illnesses who are using the toy, facilitating social bonding between the children. Social bonding may also be increased by allowing systems associated with two or more different children to interact. When two toys are located within a preset range, proximity sensors 20 (FIG. 2) may send a signal to activate the microprocessor 50 to trigger a pre-programmed response using the screen 55, actuators 22, and speaker 60 to produce an audio and visual response. In this way, the toy may increase interaction among children suffering from chronic diseases.

In the case of a child diagnosed with asthma, the toy may be equipped at least with an inhaler 105 and a expiratory flow meter 106. The inhaler and flow meter may be used to manage the symptoms displayed by the toy. The toy may be programmed to facilitate the child exercising with the toy, thus inducing asthmatic symptoms that may be cared for with the inhaler. The flow meter may function to periodically measure the lung function of the system. Data about the child's inhaler compliance could be logged by the toy and later uploaded to a computer for use by doctors, parents, and the affected children. Alternatively, such data may be transmitted wirelessly, by WiFi or Bluetooth protocols, for example, on a real-time basis.

In the case of a child diagnosed with diabetes, the toy 10 may be equipped with and interact with, among other things, an insulin pen 107, insulin pump 108, CGM device 109 and accompanying replica food articles. A child may care for the toy by feeding it a well balanced diet and injecting insulin as needed, using the insulin pen 21 and pump 20. The CGM device 109 may be used as an educational tool for how food and insulin affect blood sugar within the body.

Existing diabetes management tools may be further designed to communicate with and interface with the toy. For instance, the CGM device could be configured to communicate via wireless connection to the toy, updating the glucose level of the toy according to the actual glucose level of the child.

In another embodiment, the toy may be provided for children with diabetes that serves as a docking station, via wired or wireless means, for their existing medical devices. Children may be able to dock their blood glucose meter into the toy to sync data and unlock special games as well as additional content.

The system or systems described herein may be implemented on any form of computer or computers and the components may be implemented as dedicated applications or in client-server architectures, including a web-based architecture, and can include functional programs, codes, and code segments. Any of the computers may comprise a processor, a memory for storing program data and executing it, a permanent storage such as a disk drive, a communications port for handling communications with external devices, and user interface devices, including a display, keyboard, mouse, etc. When software modules are involved, these software modules may be stored as program instructions or computer readable codes executable on the processor on a computer-readable media such as read-only memory (ROM), random-access memory (RAM), CD-ROMs, magnetic tapes, floppy disks, and optical data storage devices. The computer readable recording medium can also be distributed over network coupled computer systems so that the computer readable code is stored and executed in a distributed fashion. This media is readable by the computer, stored in the memory, and executed by the processor.

All references, including publications, patent applications, and patents, cited herein are hereby incorporated by reference to the same extent as if each reference were individually and specifically indicated as incorporated by reference and were set forth in its entirety herein.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The embodiments herein may be described in terms of functional block components and various processing steps. Such functional blocks may be realized by any number of hardware and/or software components that perform the specified functions. For example, the described embodiments may employ various integrated circuit components, e.g., memory elements, processing elements, logic elements, look-up tables, and the like, which may carry out a variety of functions under the control of one or more microprocessors or other control devices. Similarly, where the elements of the described embodiments are implemented using software programming or software elements the invention may be implemented with any programming or scripting language such as C, C++, Java, assembler, or the like, with the various algorithms being implemented with any combination of data structures, objects, processes, routines or other programming elements. Functional aspects may be implemented in algorithms that execute on one or more processors. Furthermore, the embodiments of the invention could employ any number of conventional techniques for electronics configuration, signal processing and/or control, data processing and the like. The words "mechanism" and "element" are used broadly and are not limited to mechanical or physical embodiments, but can include software routines in conjunction with processors, etc.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical".

The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings. Expressions such as "at least one of," when preceding a list of elements, modify the entire list of elements and do not modify the individual elements of the list.

The use of the terms "a" and "an" and "the" and similar referents in the context of describing the invention (especially in the context of the following claims) should be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Finally, the steps of all methods described herein are performable in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. Numerous modifications and adaptations will be readily apparent to those skilled in this art without departing from the spirit and scope of the invention.

What is claimed is:

1. An interactive children's toy serving as a surrogate by emulating medical condition characteristics of a child and providing responses and output to educate users about the medical condition, comprising:
    a microprocessor and a memory;
    a plurality of sensors electrically connected to the microprocessor;
    a plurality of output systems connected to the microprocessor;
    a replica device representing a medical device monitoring the child, wherein the medical device is configured to collect health status data of the child,
    wherein the microprocessor is programmed to:
        receive information from the plurality of sensors that is representative of a treatment for the medical condition,
        send signals to the output systems consistent with a reaction to the treatment for the medical condition characteristics of the child;
        receive health status data of the child from the medical device monitoring the child and being represented by the replica device; and
        synchronize health status data of the replica device with the health status data received from the medical device.

2. The toy of claim 1, wherein the microprocessor is programmed to provide feedback through the output systems that evolves based upon a series of signals received by the sensors over a period of time.

3. The toy of claim 1, wherein the plurality of sensors include at least one of: color sensors, image sensors, proximity switches, light sensors, heat sensors, audio sensors, tactile sensors, magnetic sensors, movement sensors, and radio frequency sensors.

4. The toy of claim 1, wherein the output systems include at least one of: an audio speaker, a light source, and a motor capable of moving or vibrating the toy or an extremity of the toy.

5. The toy of claim 4, wherein the audio speaker produces at least one sound selected from the group consisting of: coughing sounds, wheezing sounds, speech, heart sounds, bowel sounds, breathing, lung sounds, moaning or groaning sounds, and crying sounds.

6. The toy of claim 4, wherein the light source is heart-shaped, generates heat, and repeatedly turns on then off at a set frequency.

7. The toy of claim 1, wherein the medical condition includes at least one of: asthma, allergies, cystic fibrosis, diabetes, cancer, cerebral palsy, sickle cell anemia, AIDS, epilepsy, spina bifida, pulmonary hypertension, sleep apnea, liver cirrhosis, hyperthyroidism, chronic obstructive pulmonary disease, congenital heart problems, ADHD, autism, Obsessive Compulsive Disorder, obesity, depression, anxiety, and stress.

8. The toy of claim 1, further comprising real or replica medical devices that interact with at least one of the sensors.

9. The toy of claim 8, wherein the medical devices include at least one of: metered-dose inhalers, dry powder inhalers, nebulizers, analgesic inhalers, syringes, stethoscopes, gastric feeding tubes, insulin pumps, glucose monitoring systems, heart rate monitors, pulse oximeters, pedometers, galvanic skin response measurement systems, gaze tracking systems, and electroencephalogram monitoring systems.

10. The toy of claim 8, further comprising a plurality of patches disposed on a surface of the toy and at least one of the sensors being located beneath the patches to detect interaction with the medical devices, wherein the patches are coded with symbols to educate regarding injection site rotation.

11. The toy of claim 1, further comprising a book containing text relating to the medical condition, wherein the text of the book is stored in the memory and further wherein the microprocessor is programmed to audibly speak the stored text through the audio speaker.

12. The toy of claim 1, further comprising
a plurality of replica food articles that interact with at least one of the sensors;
programming for the microprocessor that receives signals from the sensors relating to the replica food articles that senses at least one of the color, weight, size, shape, composition and type of the replica food article.

13. The toy of claim 1, further comprising an external data storage component communicatively coupled to the toy to store treatment compliance data.

14. The toy of claim 1, further comprising a detachable updateable core comprising a microcontroller, a plurality of batteries, and a plurality of updateable core sensors and a pedometer.

15. The toy of claim 1, further comprising a communications interface for connection to a personal computer, mobile device, or medical device, such that data is transferable between the toy and the personal computer, mobile device, or medical device.

16. The toy of claim 15, wherein the personal computer, mobile device, or medical device further comprises:
a data collection system;
a toy interaction tracking system; and
a medical professional communication system allowing information about the child to be sent to the medical professional.

17. The toy of claim 1, further comprising a wireless communications interface to a second toy as claimed in claim 1, wherein the first toy detects the proximity of the second toy and wirelessly transfers and receives data from the second toy.

18. The toy of claim 1, wherein the replica medical device is a digital replica of a medical device.

19. The toy of claim 18, wherein the digital replica of the medical device is stored on a computing device, and the surrogate is a digital character stored on the computing device.

20. The toy of claim 1, wherein the plurality of sensors is wirelessly connected to the microprocessor.

21. The toy of claim 1, wherein the microprocessor receives the health status data from the medical device wirelessly.

* * * * *